United States Patent [19]

Hong et al.

[11] Patent Number: 5,243,000

[45] Date of Patent: * Sep. 7, 1993

[54] PROCESS FOR MAKING POLYVINYL CHLORIDE USING PHENOTHIAZINE OLIGOMER

[75] Inventors: Paul O. Hong, Wayne; Raymond C. DeWald, Douglassville, both of Pa.

[73] Assignee: Occidental Chemical Corporation, Niagara Falls, N.Y.

[*] Notice: The portion of the term of this patent subsequent to Aug. 1, 2006 has been disclaimed.

[21] Appl. No.: 424,435

[22] Filed: Oct. 20, 1989

Related U.S. Application Data

[63] Continuation-in-part of Ser. No. 344,169, Feb. 16, 1989, Pat. No. 4,960,885, which is a continuation-in-part of Ser. No. 213,743, Jun. 30, 1988, Pat. No. 4,853,446, which is a continuation-in-part of Ser. No. 79,315, Jul. 30, 1987, Pat. No. 4,855,424.

[51] Int. Cl.⁵ .............................................. C08F 2/16
[52] U.S. Cl. ......................................... 526/74; 526/62; 526/344.2
[58] Field of Search ............................................. 526/74

[56] References Cited

U.S. PATENT DOCUMENTS

| | | | |
|---|---|---|---|
| 2,415,252 | 2/1947 | Levi . | |
| 2,528,092 | 10/1950 | Smith et al. . | |
| 2,981,722 | 4/1961 | Enk et al. . | |
| 3,669,946 | 6/1972 | Koyunagi | 526/62 |
| 3,997,707 | 12/1976 | Aruga | 526/62 |
| 4,180,634 | 12/1979 | Koyanagi | 526/62 |
| 4,229,510 | 10/1980 | Watarai et al. . | |
| 4,377,672 | 3/1983 | Geschonke et al. . | |
| 4,465,881 | 8/1984 | Miller et al. . | |
| 4,528,337 | 7/1985 | Kreilein et al. | 526/64 |
| 4,529,500 | 7/1985 | Miller et al. . | |
| 4,565,834 | 1/1986 | Buysch et al. . | |
| 4,845,174 | 7/1989 | Amano | 526/62 |
| 4,853,446 | 8/1989 | DeWald | 526/205 |
| 4,855,424 | 8/1989 | Hong et al. | 544/35 |

OTHER PUBLICATIONS

Chemical Abstracts (1983) vol. 98:144251d, Romanovich et al.

*Primary Examiner*—Christopher Henderson
*Attorney, Agent, or Firm*—Wayne A. Jones; Richard D. Fuerle

[57] ABSTRACT

A microsuspension polymerization process for polymerizing vinyl chloride and optional comonomers to polyvinyl chloride and optional copolymers is disclosed which comprises conducting the polymerization in a tubular reaction zone without agitation in the presence of a compound having the formula

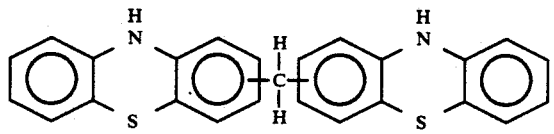

8 Claims, No Drawings

PROCESS FOR MAKING POLYVINYL CHLORIDE USING PHENOTHIAZINE OLIGOMER

This is a continuation-in-part of application Ser. No. 344,169, filed Feb. 16, 1989, now U.S. Pat. No. 4,960,885 which is a continuation-in-part of U.S. application Ser. No. 213,743, filed Jun. 30, 1988 now U.S. Pat. No. 4,853,446, which was a continuation-in-part of application Ser. No. 079,315, filed Jul. 30, 1987, now U.S. Pat. No. 4,855,424.

BACKGROUND OF INVENTION AND INFORMATION DISCLOSURE STATEMENT

U.S. Pat. Nos. 4,853,446 and 4,855,424 disclose and claim novel compounds and compositions which have been found to inhibit the build-up of scale on the walls of vinyl chloride polymerization reactors. Such reactor scale interferes with heat transfer, and consumes valuable monomer which is lost to the final products, and results in the increase in waste product that must be disposed of safely.

The above listed patents disclose the use of the additive of the invention in various polymerization reactions for making polyvinyl chloride including emulsion polymerization, bulk or mass polymerization, suspension polymerization and microsuspension polymerization.

It is the purpose of this invention to provide an improved microsuspension process to demonstrate reduced reactor wall fouling or scale deposits, as well as flocculated material, during polymerization of vinyl chloride and other monomers. The microsuspension process of the invention is characterized in that the polymerization is conducted in a tubular reaction zone without agitation. The microsuspension process used in the process of this invention is disclosed in U.S. Pat. Nos. 2,981,722; 4,377,672, and 4,528,337, the disclosures of which are incorporated herein by reference.

SUMMARY OF THE INVENTION

The purposes of this invention are accomplished by providing a microsuspension polymerization process for polymerizing vinyl chloride and co-monomers to polyvinyl chloride and co-polymers, which comprises conducting the polymerization in a tubular reaction zone without agitation, in the presence of a compound having the formula

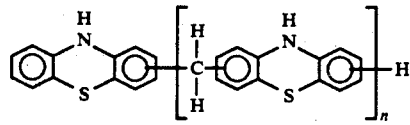

wherein n has an average value of about one to about five.

The purposes of this invention are accomplished by providing a microsuspension polymerization process for polymerizing vinyl chloride and co-monomers to polyvinyl chloride and co-polymers which comprises conducting the polymerization in a tubular reaction zone without agitation, in the presence of a composition having the formula

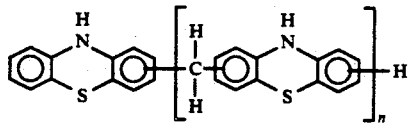

wherein n has an average value of about one to about five.

PREFERRED EMBODIMENTS OF THE INVENTION

The compounds (dimers) and compositions (dimer together with higher oligomers) that form the basis of the invention are disclosed and claimed in U.S. Pat. Nos. 4,853,446 and 4,855,424, the disclosures of which are incorporated herein by reference. The processes for manufacturing the compounds and compositions are also disclosed in these patents. Processes suitable for use in preparing the compounds and compositions are disclosed in copending application Ser. No. 07/424,415, filed on even date herewith, the disclosure of which is incorporated herein by reference.

The microsuspension process employed in the process of the invention is disclosed in U.S. Pat. Nos. 2,981,722; 4,377,672, and 4,528,337, the disclosures of which are incorporated herein by reference. In this process, the tubular reactor is preferentially vertically elongated and preferably has a substantially circular cross-section.

The foregoing compounds (dimers) and compositions of the invention (dimer together with higher oligomers) are utilized as disclosed as follows in the reduction or elimination of scale and flocculated material in a reaction vessel and reactor components such as an agitator, used for the polymerization of vinyl chloride. The compositions of the invention are also useful in the polymerization of vinyl chloride with α-olefinically, more specifically ethylenically unsaturated comonomers in a proportion of up to about 80 mole percent comonomers, more specifically, up to about 40 mole percent comonomers. Such comonomers include vinyl acetate, and other ethylenically unsaturated monomers that are well known in the art.

The dimer alone or together with higher oligomers is dissolved in a suitable solvent such as tetrahydrofuran (THF) in a proportion of about 0.3 to about 1 weight percent. The resulting solutions are then brushed or sprayed on the reactor walls, on the reactor agitator, and inside the reactor head. The polymerization reaction mixture is inhibited from forming undesirable scale on the reactor components. Other solvents that can be employed in the application of the solutions to the reactor components include dimethylformamide (DMF), cyclohexanone and dimethylsulfoxide (DMSO).

The compounds and compositions of the invention can also be added directly to the polymerization reaction mixture, generally in a proportion of about 0.0001 to about 0.01 weight percent solids, preferably about 0.001 weight percent solids based on the weight of vinyl chloride and comonomers. The compounds and compositions of the invention can be added to the polymerization zone as dry solid or in solution in the foregoing solvents. The compounds and compositions can also be added in the wet cake form after filtering, but before drying in the manufacturing process.

The compounds and compositions of the invention are also useful in inhibiting the polymerization of monomers such as vinyl chloride or in shortstopping the polymerization of such monomers.

EXAMPLES

In the following examples and throughout the specification and claims, parts are by weight and temperatures are in degrees Celsius, unless indicated otherwise.

PREPARATION EXAMPLE A (ADDITIVE COMPOSITION)

200 grams of phenothiazine were dissolved in 500 cc of tetrahydrofuran with stirring at room temperature. A solution of 98 cc of 96 percent sulfuric acid and 50 cc of 37 weight percent formaldehyde solution in 500 cc of methanol was added slowly to the phenothiazine solution with continued stirring. The mixture was refluxed with stirring for 1½ hours. The sulfuric acid was neutralized by the addition of 87 grams of sodium hydroxide in 250 cc of water. The slurry was filtered, washed three times with 500 cc portions of a 50/50 by volume mixture of tetrahydrofuran and methanol to remove unreacted phenothiazine. The solvent wetcake was then washed 4 times with 1 liter portions of 70° C. water to remove salts and solvents. This wetcake was dried for 16 hours at 60° C. in an oven. The dried material was ready for use for reactor wall coating.

EXAMPLE 1 (Control)

2320 grams of vinyl chloride together with 2680 grams of deionized water, 7.3 grams of tridecyl alcohol, 46.4 grams of ammonium salt of dihydroxy stearic acid, 2.28 grams of lauroyl peroxide and 3.2 grams of 25% bis(2-ethyl hexyl) peroxydicarbonate were mixed for 30 minutes in a premix tank, then homogenized for 15 minutes through a high shear Ross mixer. The monomer emulsion was introduced into an evacuated tubular autoclave (H=45 inches, D=3 inches) and heated to 50° C. 16 hours after the reaction temperature had been reached, polymerization was complete which could be detected by the drop in pressure. The pressure was released and the polyvinyl chloride latex was drained off. The latex was stable and had a solids content of 44 percent. The autoclave wall was uniformly coated with polyvinyl chloride polymer residue which was collected and found to weigh 20.9 grams.

EXAMPLE 2

In this example, the internal wall of a tubular autoclave was coated with a solution containing 0.1 gram of the composition prepared as in Example A, 0.2 gram of phytic acid, 5.0 grams of THF and 5.0 grams of DMF. The coating material was air dried for 2 hours with air blowing on the coating surface. Then a batch of polyvinyl chloride was prepared as in Example 1. The latex obtained was stable and had a solids content of 44 percent. There was only 2 grams of scale built up on the autoclave wall.

EXAMPLE 3 (Control)

2320 grams of vinyl chloride together with 2680 grams of deionized water, 55 grams of 30% sodium lauryl sulfate, 4.5 ml. of calcium versene, 2.28 grams of lauroyl peroxide and 3.2 grams of 25 percent bis (2-ethyl hexyl) peroxydicarbonate were mixed for 30 minutes in a premix tank, then homogenized for 15 minutes through a high shear Ross mixer. The monomer emulsion was polymerized as in Example 1. The latex was stable and had a solids content of 45 percent. The autoclave wall was uniformly coated with polyvinyl chloride polymer residue which was collected and found to weigh 23.0 grams.

EXAMPLE 4

In this example, the internal wall of a tubular autoclave was coated with a solution containing 0.1 gram of the composition prepared as in Example A, 0.2 gram of phytic acid, 5.0 grams of THF and 5.0 grams of DMF. The coating material was air dried for 2 hours with air blowing through the tube. Then a batch of polyvinyl chloride was prepared as in Example 3. The latex obtained was stable and had a solids content of 44 percent. There were only trace amounts of scale buildup on the autoclave wall.

We claim:

1. In a microsuspension polymerization process for polymerizing vinyl chloride to polyvinyl chloride or vinyl chloride and a copolymerizable monomer to vinyl chloride copolymer, wherein the polymerization is conducted in a tubular reaction zone without agitation, the improvement comprising conducting the polymerization in the presence of a composition having the formula

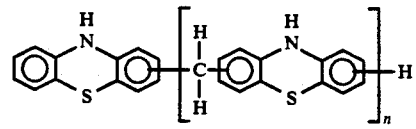

wherein n has an average value of about one to about five.

2. A process for the manufacture of vinyl chloride polymer or copolymer by microsuspension polymerization of vinyl chloride or vinyl chloride and up to 40 percent by weight, based on the total monomer content, of α-olefinically unsaturated monomers copolymerizable with vinyl chloride comprising the steps of:
   (1) dispersing the monomer or the monomer mixture in water,
   (2) homogenizing the resulting dispersion,
   (3) polymerizing the resulting homogenized dispersion in a vertically elongated reaction zone at an elevated temperature and elevated pressure, and
   (4) recovering said vinyl chloride polymer or copolymer wherein no mechanical agitation of the dispersion takes place during polymerization, and
wherein the polymerization is carried out in the presence of a composition of the formula wherein n has an average value of about one to about five.

3. The process of claim 2 wherein a solution of said compound in a solvent is coated on the walls of the polymerization zone.

4. The process of claim 2 wherein said compound is added to the polymerization zone in a proportion of about 0.0001 to about 0.01 weight percent solids based on the weight of vinyl chloride and comonomers.

5. The process of claim 2 wherein said vertically elongated reaction area has a substantially circular cross-section.

6. The improvement of claim 1 wherein n has an average value of about 1.

7. The process of claim 1 wherein a solution of said compound in a solvent is coated on the walls of the polymerization zone.

8. The process of claim 1 wherein said compound is added to the polymerization zone in a proportion of about 0.0001 to about 0.01 weight percent solids based on the weight of vinyl chloride and comonomers.

* * * * *